(12) United States Patent
Soerens et al.

(10) Patent No.: US 6,737,491 B2
(45) Date of Patent: May 18, 2004

(54) ABSORBENT BINDER COMPOSITION AND METHOD OF MAKING SAME

(75) Inventors: Dave Allen Soerens, Neenah, WI (US); Jason Matthew Laumer, Appleton, WI (US); Kambiz Bayat Makoui, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 24 days.

(21) Appl. No.: 10/206,883

(22) Filed: Jul. 26, 2002

(65) Prior Publication Data
US 2004/0019169 A1 Jan. 29, 2004

(51) Int. Cl.$^7$ .............................................. C08F 130/08

(52) U.S. Cl. ................ 526/279; 526/271; 526/277; 526/287; 526/307.6; 526/320; 526/328.5; 526/329.6; 526/332

(58) Field of Search ................. 526/271, 277, 526/279, 287, 307.6, 320, 328.5, 329.6, 332

(56) References Cited

U.S. PATENT DOCUMENTS

| | | | |
|---|---|---|---|
| 3,617,362 A | * 11/1971 | Bemmels et al. ........... 117/122 |
| 3,963,605 A | 6/1976 | Seabourn |
| 4,251,643 A | 2/1981 | Harada et al. |
| 4,291,136 A | 9/1981 | Keogh |
| 4,328,323 A | 5/1982 | Keogh |
| 4,343,917 A | 8/1982 | Keogh |
| 4,353,997 A | 10/1982 | Keogh |
| 4,369,289 A | 1/1983 | Keogh |
| 4,408,011 A | 10/1983 | Barnabeo |
| 4,434,272 A | 2/1984 | Keogh |
| 4,440,907 A | 4/1984 | Keogh |
| 4,446,279 A | 5/1984 | Keogh |
| 4,459,396 A | 7/1984 | Yamasaki et al. |
| 4,489,029 A | 12/1984 | Keogh et al. |
| 4,493,924 A | 1/1985 | Rifi |
| 4,526,930 A | 7/1985 | Keogh |
| 4,551,504 A | 11/1985 | Barnabeo |
| 4,575,535 A | 3/1986 | Keogh |
| 4,579,913 A | 4/1986 | Keogh |
| 4,593,071 A | 6/1986 | Keogh |
| 4,676,820 A | 6/1987 | Le Sergent et al. |
| 4,753,993 A | 6/1988 | Keogh |
| 4,767,820 A | 8/1988 | Keogh |
| 4,921,136 A | 5/1990 | Roggenburg, Jr. |

(List continued on next page.)

FOREIGN PATENT DOCUMENTS

| | | |
|---|---|---|
| CA | 756190 | 4/1967 |
| EP | 0 132 910 A2 | 2/1985 |
| EP | 0 705 861 A1 | 4/1996 |
| EP | 0 844 265 A1 | 5/1998 |
| EP | 0 992 252 | 4/2000 |
| EP | 1 013 291 A1 | 6/2000 |
| EP | 1 059 320 A2 | 12/2000 |
| EP | 1 199 059 | 4/2002 |
| WO | 99/57201 | 11/1999 |
| WO | WO 02/053664 A2 | 7/2002 |

Primary Examiner—Helen L. Pezzuto
(74) Attorney, Agent, or Firm—Pauley Petersen & Erickson

(57) ABSTRACT

An absorbent binder composition including a monoethylenically unsaturated polymer, such as carboxylic acid, sulphonic acid, or phosphoric acid, or salts thereof, and an acrylate or methacrylate ester that contains an alkoxysilane functionality, or a monomer capable of co-polymerization with a compound containing a trialkoxy silane functional group and subsequent reaction with water to form a silanol group. The absorbent binder composition is particularly suitable for use in manufacturing absorbent articles. A method of making the absorbent binder composition includes preparing a monomer solution, adding the monomer solution to an initiator solution, and activating a polymerization initiator within the initiator solution.

68 Claims, 1 Drawing Sheet

U.S. PATENT DOCUMENTS

| | | |
|---|---|---|
| 4,940,646 A | 7/1990 | Pawlowski |
| 5,047,476 A | 9/1991 | Keogh |
| 5,089,564 A * | 2/1992 | Bullen ................. 525/370 |
| 5,112,919 A | 5/1992 | Furrer et al. |
| 5,145,906 A | 9/1992 | Chambers et al. |
| 5,196,470 A | 3/1993 | Anderson et al. |
| 5,204,404 A | 4/1993 | Werner, Jr. et al. |
| 5,364,382 A | 11/1994 | Latimer et al. |
| 5,389,728 A | 2/1995 | Prejean |
| 5,532,350 A | 7/1996 | Cottrell et al. |
| 5,656,132 A | 8/1997 | Farrington, Jr. et al. |
| 5,853,867 A | 12/1998 | Harada et al. |
| 5,911,937 A | 6/1999 | Hekal |
| 5,932,668 A | 8/1999 | Friebe et al. |
| 6,020,171 A | 2/2000 | Watson |
| 6,054,523 A | 4/2000 | Braun et al. |
| 6,110,533 A | 8/2000 | Coté et al. |
| 6,403,857 B1 | 6/2002 | Gross et al. |
| 6,417,425 B1 | 7/2002 | Whitmore et al. |
| 6,596,402 B2 * | 7/2003 | Soerens et al. ............. 428/447 |
| 2002/0090453 A1 | 7/2002 | Muthiah et al. |

* cited by examiner

ABSORBENT BINDER COMPOSITION AND METHOD OF MAKING SAME

BACKGROUND OF THE INVENTION

This invention is directed to an absorbent binder or coating composition, and a method of making the absorbent binder or coating composition.

Adhesives, or binders, are a necessary element of many absorbent products. While adhesives beneficially hold products together, adhesives may also have a tendency to interfere with the absorbency of fluids in absorbent products. Adhesives are typically hydrophobic and therefore are not conducive to absorbency or liquid transfer functions. Furthermore, most adhesives are non-absorbent and thus serve no liquid retention function.

Hydrophilic adhesives are known, such as adhesives formulated from water-soluble polymers such as poly(vinyl alcohol), poly(vinyl methyl ether), poly(vinyl pyrrolidone), poly(ethylene oxide), or cellulose derivatives such as hydroxypropyl cellulose. Dextrans, starches and vegetable gums have been used to provide hydrophilic adhesives. These materials provide adhesion under dry conditions. However, upon exposure to aqueous fluids, these materials lose bonding capability because they are substantially soluble in aqueous fluids.

A known approach for making hydrophilic adhesives more functional upon exposure to aqueous fluid is to crosslink the water-soluble polymers. As a result of crosslinking, the material becomes swellable, and no longer soluble, in aqueous fluid. However, crosslinked polymers are difficult to apply to substrates or to establish intimate contact with surfaces because the crosslinked polymers are solid materials and have little or no ability to flow.

What is therefore needed is a hydrophilic binder or coating that has latent crosslinking capability. Such binder or coating could be easily applied, like a water-soluble polymer, since the hydrophilic binder or coating would be capable of flow prior to crosslinking. Latent crosslinking capability would also provide a simple means of crosslinking the polymer after the polymer has established intimate contact with substrates or has formed a desired final shape or form.

Post-application crosslinking is well known. Typical means of inducing the formation of crosslinks include high temperature "curing" or exposure to radiation, such as ultraviolet or gamma radiation. Another known means of post-application crosslinking is moisture-induced crosslinking.

Recent development efforts have provided coating materials for a variety of uses. For example, U.S. Pat. No. 6,054,523, to Braun et al., describes materials that are formed from organopolysiloxanes containing groups that are capable of condensation, a condensation catalyst, an organopolysiloxane resin, a compound containing a basic nitrogen, and polyvinyl alcohol. The materials are reported to be suitable for use as hydrophobic coatings and for paints and sealing compositions.

Anderson et al., in U.S. Pat. No. 5,196,470, reported an alcohol-based, water-soluble binder composition. Because this composition is water-soluble and not cross-linked, it has no absorbency.

Others have reported the production of graft copolymers having silane functional groups that permitted the initiation of cross-linking by exposure to moisture. Prejean (U.S. Pat. No. 5,389,728) describes a melt-processible, moisture-curable graft copolymer that was the reaction product of ethylene, a 1–8 carbon alkyl acrylate or methacrylate, a glycidyl containing monomer such as glycidyl acrylate or methacrylate, onto which has been grafted N-tert-butylaminopropyl trimethoxysilane. The resulting copolymers were reported to be useful as adhesives and for wire and cable coatings.

Furrer et al., in U.S. Pat. No. 5,112,919, reported a moisture-crosslinkable polymer that was produced by blending a thermoplastic base polymer, such as polyethylene, or a copolymer of ethylene, with 1-butene, 1-hexene, 1-octene, or the like; a solid carrier polymer, such as ethylene vinylacetate copolymer (EVA), containing a silane, such as vinyltrimethoxysilane, and a free-radical generator, such as an organic peroxide; and heating the mixture. The copolymers could then be cross-linked by reaction in the presence of water and a catalyst, such as dibutyltin dilaurate, or stannous octoate.

U.S. Pat. No. 4,593,071 to Keough reported moisture cross-linkable ethylene copolymers having pendant silane acryloxy groups. The resultant cross-linked polymers were reported to be especially resistant to moisture and to be useful for extruded coatings around wires and cables. The same group has reported similar moisture curable polymers involving silanes in U.S. Pat. Nos. 5,047,476, 4,767,820, 4,753,993, 4,579,913, 4,575,535, 4,551,504, 4,526,930, 4,493,924, 4,489,029, 4,446,279, 4,440,907, 4,434,272, 4,408,011, 4,369,289, 4,353,997, 4,343,917, 4,328,323, and 4,291,136.

U.S. Pat. No. 5,204,404 to Werner reported crosslinkable hydrophobic acrylate ester copolymers including 0.1 to 10% acrylic acid. The resultant cross-linked polymers were reported to be useful for painting and refinishing the exterior of automobiles.

These examples of moisture-induced crosslinking are applied to substantially hydrophobic polymers. Since the cured products of these formulations are reported to be useful for coverings for wire and cable, and for non-conductive coatings for electrical conductors, and for painting and refinishing the exterior of automobiles, it would be expected that they are durable coatings for which properties such as water absorbency would be a disadvantage.

There is thus a need within the field of absorbent products for absorbent binders, adhesives, or coatings. Furthermore, there is a need within the field of absorbent products for such absorbent binders, adhesives, or coatings that can be prepared by post-application, moisture-induced crosslinking of hydrophilic polymers.

SUMMARY OF THE INVENTION

In response to the discussed difficulties and problems encountered in the prior art, a new absorbent composition, useful as a binder, adhesive, or coating material, has been discovered. The absorbent composition includes a hydrophilic polymer which has the capability of post-application, moisture-induced crosslinking. This capability provides for absorbent products having greater absorbent capacity.

The absorbent binder composition includes at least 15 mass percent monoethylenically unsaturated polymer, such as carboxylic acid, sulphonic acid, phosphoric acid, or salts thereof, and an acrylate or methacrylate ester that contains an alkoxysilane functionality. Upon exposure to water, the alkoxysilane functionality forms a silanol functional group which condenses to form a crosslinked polymer. Thus, the absorbent binder composition provides enhanced adhesion in a wet condition, as well as absorbency.

The absorbent binder composition suitably has a glass transition temperature below about 30 degrees Celsius, or below about 10 degrees Celsius, and a bending modulus lower than the bending modulus of a substrate to which the composition is applied. The absorbent binder composition may be used in the manufacture of absorbent products, and therefore may be applied to such substrates as nonwoven webs, woven webs, knitted fabrics, cellulose tissue, plastic film, stranded composites, elastomer net composites, or any other suitable substrates. Examples of suitable types of plastic film substrates include those made of polypropylene, low density polyethylene, high density polyethylene, linear low density polyethylene, and ultra low density polyethylene. Examples of absorbent articles in which the absorbent binder composition may be used include diapers, diaper pants, training pants, feminine hygiene products, incontinence products, swimwear garments, and the like.

The absorbent binder composition of the invention can be made by polymerizing monoethylenically unsaturated monomers, one of which contains an alkoxysilane functionality. The polymerization may be induced by a variety of initiation techniques including thermal initiation, radiation initiation, or redox chemical reactions. Various types of effective radiation initiation include ultraviolet, microwave, and electron-beam radiation. The initiator generates free radicals to cause polymerization of the monomers. The resultant copolymer includes latent moisture-induced crosslinking capability by incorporation of the alkoxysilane functionality. This copolymer may be applied, in a flowable state, to a substrate or other end use application. Moisture-induced crosslinking may be accomplished through hydrolysis of the alkoxysilane and subsequent condensation upon removal of the solvent from the substrate, either by evaporation of the solvent from the substrate or using any other effective technique. Alternatively, the hydrolysis of the alkoxysilane and subsequent condensation may occur after solvent removal by exposure of the coating to moisture in ambient air.

With the foregoing in mind, it is a feature and advantage of the invention to provide an absorbent binder composition, and a method of making such absorbent binder compositions.

BRIEF DESCRIPTION OF THE DRAWINGS

These and other objects and features of this invention will be better understood from the following detailed description taken in conjunction with the drawings, wherein.

DEFINITIONS

Figure 1:
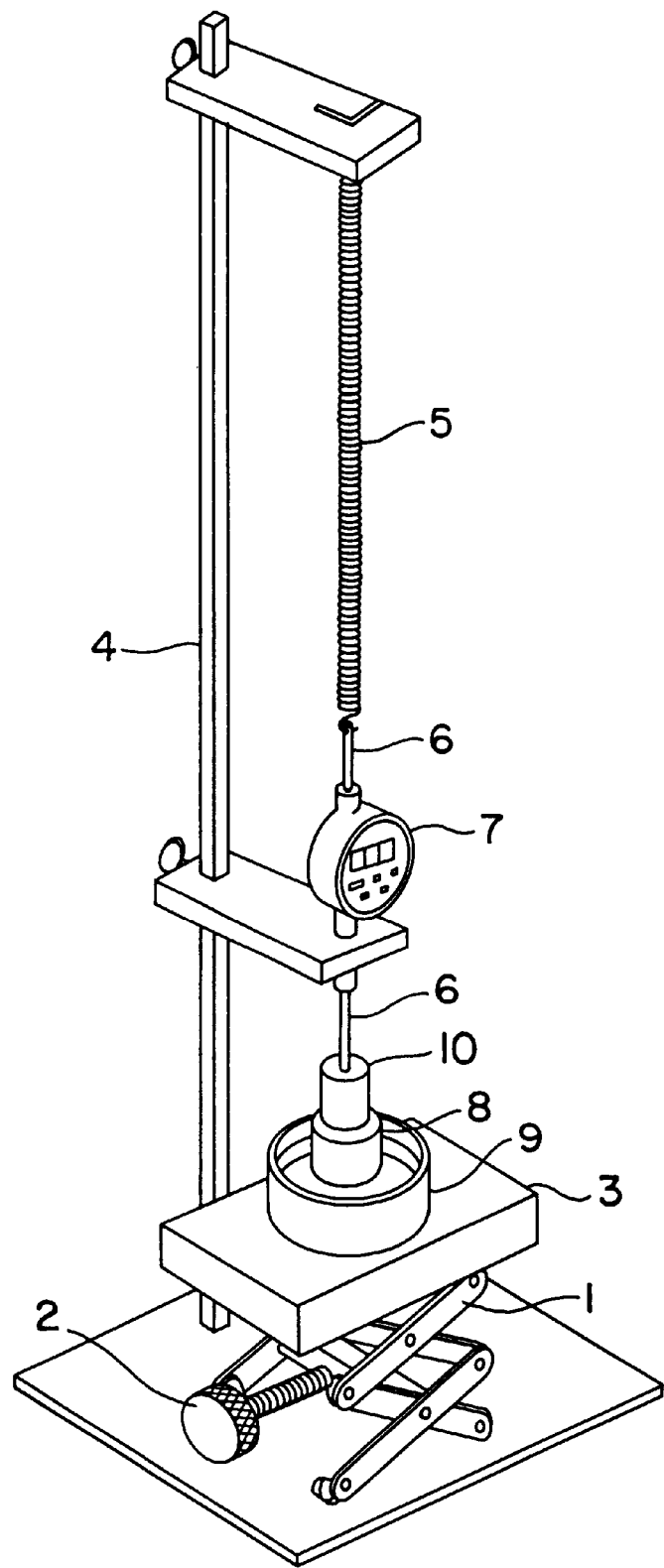
FIG. 1 is an illustration of equipment for determining the Absorbency Under Load (AUL) of absorbent material.

Within the context of this specification, each term or phrase below will include the following meaning or meanings.

"Binder" includes materials which are capable of attaching themselves to a substrate or are capable of attaching other substances to a substrate.

"Feminine hygiene products" include sanitary pads and napkins, as well as tampons and interlabial feminine hygiene products.

"Fluid" refers to a substance in the form of a liquid or gas at room temperature and atmospheric pressure.

"High density polyethylene (HDPE)" refers to a polyethylene having a density of about 0.95 g/cm$^3$ or greater.

"Knife over roll coating" refers to a process in which a knife is positioned, with a specified gap, above a substrate that is moving beneath the knife on a moving roll. In this manner, the knife spreads a specified thickness of coating material onto the substrate.

"Layer" when used in the singular can have the dual meaning of a single element or a plurality of elements.

"Linear low density polyethylene (LLDPE)" refers to polymers of ethylene and higher alpha-olefin comonomers such as $C_3$–$C_{12}$ comonomers, and combinations thereof, having a density of about 0.900 to 0.935 g/cm$^3$.

"Low density polyethylene (LDPE)" refers to a polyethylene having a density between about 0.91 and about 0.925 g/cm$^3$.

"Modifying agent" refers to a substance that may be added to a composition to modify the physical properties of the composition, such as the color or texture of the composition.

"Nonwoven" or "nonwoven web" refers to materials and webs or material having a structure of individual fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Personal care product" includes diapers, diaper pants, training pants, swim wear, absorbent underpants, adult incontinence products, feminine hygiene products, and the like.

"Roll printing" or "roll coating" refers to a process in which the application of a deposited material, generally as a paste, onto a substrate is carried out by transferring the deposited material from a roll onto the substrate in a more or less uniform layer using one or more rolls, which may be engraved, and a pool cylinder. A doctor blade is used to scrape any excess deposited material from the rolls or substrate. The doctor blade may be flat or have a patterned edge such as slots or ridges.

"Rotary screen printing" or "rotary screen coating" refers to a process that is a combination of roll printing or coating and screen printing or coating.

"Screen printing" or "screen coating" refers to a method of applying a deposited material by forcing the material to be deposited through a screen that may have uniform openings or patterned openings.

"Stranded composites" refer to sheets of material to which strands of an elastomeric material are adhered to create an elastomeric composite.

"Superabsorbent" refers to a water-swellable, water-insoluble organic or inorganic material capable, under the most favorable conditions, of absorbing at least about 15 times its weight and, more desirably, at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers. "Ultra low density polyethylene (ULDPE)" refers to polymers of ethylene and higher alpha-olefin comonomers such as $C_3$–$C_{12}$ comonomers, and combinations thereof, having a density of about 0.860 to less than 0.900 g/cm$^3$.

DESCRIPTION OF PREFERRED EMBODIMENTS

The present invention is directed to an absorbent binder composition that includes a hydrophilic polymer having the capability of post-application, moisture-induced crosslinking. The present invention also includes a method of making and applying such an absorbent binder composition. The absorbent binder composition can provide fluid retention properties in addition to adhesive properties. Thus, the absorbent binder composition is particularly suitable for use in forming absorbent products.

More specifically, the binder composition includes at least 15 mass percent monoethylenically unsaturated carboxylic, sulphonic or phosphoric acid or salts thereof and an acrylate or methacrylate ester that contains an alkoxysilane functionality which, upon exposure to water, forms a silanol functional group which condenses to form a crosslinked polymer.

Suitable monomers that may be included in the binder composition include carboxyl group-containing monomers: monoethylenically unsaturated mono or poly-carboxylic acids, such as (meth)acrylic acid (meaning acrylic acid or methacrylic acid; similar notations are used hereinafter), maleic acid, fumaric acid, crotonic acid, sorbic acid, itaconic acid, and cinnamic acid;

Carboxylic acid anhydride group-containing monomers: monoethylenically unsaturated polycarboxylic acid anhydrides (such as maleic anhydride);

Carboxylic acid salt-containing monomers: water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate), sodium maleate, methylamine maleate;

Sulfonic acid group-containing monomers: aliphatic or aromatic vinyl sulfonic acids (such as vinylsulfonic acid, allyl sulfonic acid, vinyltoluenesulfonic acid, stryrene sulfonic acid), (meth)acrylic sulfonic acids [such as sulfopropyl (meth)acrylate, 2-hydroxy-3-(meth)acryloxy propyl sulfonic acid];

Sulfonic acid salt group-containing monomers: alkali metal salts, ammonium salts, amine salts of sulfonic acid group containing monomers as mentioned above; and/or Amide group-containing monomers: vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth)acrylamides [such as N-methylol (meth)acrylamide, N-hydroxyethyl (meth)acrylamide], N,N-dihydroxyalkyl (meth)acrylamides [such as N,N-dihydroxyethyl (meth)acrylamide], vinyl lactams (such as N-vinylpyrrolidone).

Suitably, the amount of monoethylenically unsaturated carboxylic, sulphonic or phosphoric acid or salts thereof relative to the weight of the polymeric binder composition may range from about 15 to about 99.9 weight percent. Typically, the monoethylenically unsaturated carboxylic, sulphonic or phosphoric acid or salts thereof levels may be between about 25% and about 90% of the weight of the polymeric binder composition; particularly between about 30% and about 80% of the weight of the polymeric binder composition; or between about 50% and about 70% of the weight of the polymeric binder composition for some intended uses.

Organic monomers capable of co-polymerization with monoethylenically unsaturated carboxylic, sulphonic or phosphoric acid or salts thereof, which monomers contain a trialkoxy silane functional group or a moiety that reacts with water to form a silanol group, are useful in the practice of this invention. The trialkoxy silane functional group has the following structure:

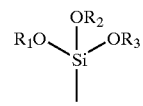

wherein $R_1$, $R_2$ and $R_3$ are alkyl groups independently having from 1 to 6 carbon atoms. The term "monomer(s)" as used herein includes monomers, oligomers, polymers, mixtures of monomers, oligomers and/or polymers, and any other reactive chemical species which is capable of co-polymerization with monoethylenically unsaturated carboxylic, sulphonic or phosphoric acid or salts thereof. Ethylenically unsaturated monomers containing a trialkoxy silane functional group are appropriate for this invention and are desired. Desired ethylenically unsaturated monomers include acrylates and methacrylates. A particularly desirable ethylenically unsaturated monomer containing a trialkoxy silane functional group is methacryloxypropyl trimethoxy silane, commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy)silane. However, it is contemplated that a wide range of vinyl and acrylic monomers having trialkoxy silane functional groups or a moiety that reacts easily with water to form a silanol group, such as a chlorosilane or an acetoxysilane, provide the desired effects are effective monomers for copolymerization in accordance with the present invention.

In addition to monomers capable of co-polymerization that contain a trialkoxy silane functional group, it is also feasible to use a monomer capable of co-polymerization that can subsequently be reacted with a compound containing a trialkoxy silane functional group or a moiety that reacts with water to form a silanol group. Such a monomer may contain, but is not limited to, an amine or an alcohol. An amine group incorporated into the co-polymer may subsequently be reacted with, for example, but not limited to, (3-chloropropyl)trimethoxysilane. An alcohol group incorporated into the co-polymer may subsequently be reacted with, for example, but not limited to, tetramethoxysilane.

The amount of organic monomer having trialkoxy silane functional groups or silanol-forming functional groups relative to the weight of the polymeric binder composition may range from about 0.1 to about 15 weight percent. Suitably, the amount of monomer should exceed 0.1 weight percent in order provide sufficient crosslinking upon exposure to moisture. Typically, the monomer addition levels are between about 0.1% and about 20% of the weight of the polymeric binder composition; particularly, between about 1.0% and about 10% of the weight of the polymeric binder composition; or between about 1.5% and about 5.5% of the weight of the polymeric binder composition for some intended uses.

Optionally, the polymeric binder may include long chain, hydrophilic monoethylenically unsaturated esters, such as poly(ethylene glycol) methacrylate having from 1 to 13 ethylene glycol units. The hydrophilic monoethylenically unsaturated esters have the following structure:

R=H or CH₃

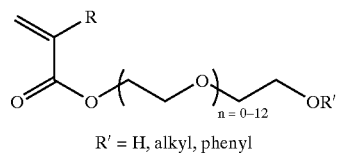

R' = H, alkyl, phenyl

The amount of monoethylenically unsaturated hydrophilic esters relative to the weight of the polymeric binder composition thereof may range from about 0 to about 75 weight percent of monomer to the weight of the polymeric binder composition. Typically, the monomer addition levels are between about 10% and about 60% of the weight of the polymeric binder composition; particularly, between about 20% and about 50% of the weight of the polymeric binder composition; or between about 30% and about 40% of the weight of the polymeric binder composition for some intended uses.

The polymeric binder composition may be prepared by adding a solution of the above monomers to an initiator solution, at a suitable temperature to generate free radicals, for example between about 50 and about 90 degrees Celsius. An initiator solution may be prepared by dissolving an initiator in a solvent. Possible solvents include, but are not limited to, alcohols such as ethanol. A variety of initiators may be useful in the practice of this invention. The polymerization initiator may be activated using a variety of methods including, but not limited to, thermal energy, ultraviolet light, redox chemical reactions. A suitable class of initiators are organic peroxides and azo compounds, with benzoyl peroxide and azobisisobutyronitrile (AIBN) as examples.

Compounds containing an O—O, S—S, or N=N bond may be used as thermal initiators. Compounds containing O—O bonds; i.e., peroxides, are commonly used as initiators for polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t-butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis (cyclohexanecarbonitrile) may be used as the initiator.

The binder composition may be applied to a substrate, such as for the purpose of adhering various components of an absorbent product to one another during the manufacturing process of absorbent products. Alternatively, the binder composition may be applied to a substrate as a coating by itself, thereby serving as an absorbency additive. The binder composition may be applied to the substrate using any suitable application process, including knife over roll coating, or roll coating, either in a continuous coverage or a patterned coverage. Printing applications are other suitable application techniques, including gravure printing, screen, and jet printing. The binder composition may also be applied to the substrate using a spray application.

Once the binder composition is applied to the substrate, crosslinking can be moisture-induced by hydrolysis and condensation of alkoxysilanes. Activation by this method can take place during solvent removal or after solvent removal by exposure to air at ambient humidity. Solvent may be removed from the substrate either by evaporating the solvent or by any other suitable technique. Recovery of the solvent is a part of the process and methods for this are widely known to those skilled in the art.

In addition, modifying agents such as compatible polymers, plasticizers, colorants, and preservatives may be incorporated in the binder composition.

For some intended uses the polymeric binder composition of this invention provides very flexible coatings and should therefore have a glass transition temperature below about 30 degrees Celsius, or below about 10 degrees Celsius, as measured by Differential Scanning Calorimetry (DSC), and a bending modulus lower than the substrate to which they are applied. Suitably, the absorbent binder composition, in combination with the substrate, has a Gurley stiffness value of less than 320 milligrams (mg), or less than 160 mg, or less than 60 mg. Suitable substrates to which the binder composition may be applied include, but are not limited to, nonwoven, woven, and knitted fabrics; cellulosic tissue sheets; plastic films, including polypropylene, low density polyethylene, high density polyethylene, linear low density polyethylene, and ultra low density polyethylene; Lycra stranded composites; and elastomer net composites.

Furthermore, crosslinked films of the polymeric binder composition are capable of absorbing at least 80 percent of their dry weight of 0.9% saline solution with no load applied during swelling. The absorbency of polymeric binder composition may range from about 80 percent of their dry weight of 0.9% saline solution to about 4000 percent of their dry weight of 0.9% saline solution with no load applied during swelling. Typical absorbency with no load applied during swelling is from 80% to 1500% of dry weight, particularly, between about 100% and about 900%; or between about 300% and about 700% of dry weight for some intended uses.

The absorbent binder composition can be used in the manufacture of absorbent products, thereby adding absorbent capacity to such absorbent products. Examples of such articles include training pants, diapers, diaper pants, feminine hygiene products, swimwear, incontinence products, absorbent toweling, other personal care or health care garments, including medical garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults.

EXAMPLES

Example 1

An initiator solution was prepared by dissolving 0.354 grams benzoyl peroxide in 300 milliliters of ethanol. The monomer solution was prepared by mixing 24.15 grams of acrylic acid (24 mass %), 73.5 grams of poly(ethylene glycol) methyl ether methacrylate (74 mass %) and 1.46 grams of 3-(trimethoxysilyl)propyl methacrylate (2 mass %) in 250 milliliters of ethanol. The initiator solution was heated in a jacketed reactor to 75 degrees Celsius with stirring. The monomer solution was added dropwise to the initiator solution. The polymerization solution was stirred and heated at 75 degrees Celsius for approximately 2 hours at which time a solution of 0.096 grams azobisisobutyronitrile (AIBN) in 30 ml ethanol was added. Stirring and heating at 75 degrees Celsius for an additional hour at which time a second solution of 0.096 grams AIBN in 30 ml ethanol was added to the polymerization solution. A third addition of 0.096 grams AIBN in 30 ml ethanol was made after one more hour at 75 degrees Celsius. Stirring and heating continued at 75 degrees Celsius for a total reaction time of about 7 hours. The reactor was cooled to 20 degrees Celsius and the solution was stirred under nitrogen atmosphere overnight. A portion of the polymer solution was dried for 16 hours at room temperature to create a sticky, water-absorbent film. A portion of the dry polymer film weighing 0.25 grams was sealed in a tea bag and immersed in 0.9% saline for 60 minutes. The tea bag containing the swollen film was centrifuged for 3 minutes at 1600 rpm (equivalent to 3 Gs) to remove free fluid. The polymer film had absorbency of 680% of 0.9 percent saline per gram of dry polymer film.

Example 2

A portion of the polymer solution from Example 1 was treated with sodium hydroxide solution to neutralize a portion (50%) of acrylic acid units in the binder polymer in order to increase the absorbency of the crosslinked film generated by drying the solution. The neutralization was done by adding 5.25 grams of an aqueous 48.5% sodium hydroxide solution to 236 grams of polymer solution (16.2% polymer) and stirring at room temperature for 5 minutes. A portion of the polymer solution was dried for 16 hours at room temperature to create a water-absorbent film. A portion of the dry polymer film weighing 0.21 grams was sealed in a tea bag and immersed in 0.9% saline for 60 minutes. The tea bag containing the swollen film was centrifuged for 3 minutes at 1600 rpm (equivalent to 3 Gs) to remove free fluid. The polymer film had absorbency of 650% of 0.9 percent saline per gram of dry polymer film.

Example 3

An initiator solution was prepared by dissolving 0.705 grams benzoyl peroxide in 300 milliliters of ethanol. The monomer solution was prepared by mixing 58.8 grams of acrylic acid (36 mass %), 100.8 grams of poly(ethylene glycol) methyl ether methacrylate (62 mass %) and 2.92 grams of 3-(trimethoxysilyl)propyl methacrylate (2 mass %) in 250 milliliters of ethanol. The initiator solution was heated in a jacketed reactor to 75 degrees Celsius with stirring. The monomer solution was added dropwise to the initiator solution. The polymerization solution was stirred and heated at 75 degrees Celsius for approximately 2 hours at which time a solution of 0.191 grams azobisisobutyronitrile (AIBN) in 30 ml ethanol was added. Stirring and heating at 75 degrees Celsius for an additional hour at which time a second solution of 0.191 grams AIBN in 30 ml ethanol was added to the polymerization solution. A third addition of 0.191 grams AIBN in 30 ml ethanol was made after one more hour at 75 degrees Celsius. Stirring and heating continued at 75 degrees Celsius for a total reaction time of about 7 hours.

Sodium hydroxide solution was used to neutralize a portion (70%) of the acrylic acid units in the binder polymer. Additional water was added to make a 10% binder solution with the solvent composition approximately 83% ethanol and 17% water.

A 9-cm by 34-cm piece of loft bonded carded web surge material made according to U.S. Pat. No. 5,364,382, manufactured by Kimberly-Clark Corporation, with a basis weight of about 45 gsm and a density of 0.04 g/cm$^3$ measured at a pressure of 0.05 psi, was immersed in about 30 grams of the binder solution to thoroughly saturate the fabric. The dry weight of the fabric was 1.78 grams. Excess fluid was squeezed out, and the saturated surge sample was dried for 4 minutes at 105 degrees Celsius in a Mathis through-air-dryer oven, available from Werner Mathis in Palmer, Pa. After drying, the coated fabric weighed 5.71 grams, so 3.93 grams of absorbent binder were applied.

The coated surge material was tested for absorbency according to the Absorbency Under Load for Composites (AULC) which is described in the Test Methods section below. The surge material coated with the absorbent binder had absorbency of 9.4 g/g at 0.03 psi, 8.7 g/g at 0.3 psi, and 8.2 g/g at 0.9 psi. Without the absorbent binder applied, the surge material has absorbency of less than 2 g/g since the fluid is substantially removed by vacuum, as described in the test method.

This example demonstrates that a fluid storage material can be made by applying the absorbent binder composition, by any suitable means, to a substrate.

TEST METHOD FOR DETERMINING ABSORBENCY UNDER LOAD FOR COMPOSITES (AULC)

The Absorbency Under Load for Composites (AULC) is a test which measures the ability of an absorbent material to absorb a liquid (such as a 0.9 weight percent aqueous solution of sodium chloride) while under an applied load or restraining force. The AULC method provides a slight positive head of fluid for the absorbent material, which is allowed to swell under a restraining load. The material is drained under vacuum at the end of the test.

The AULC test cup is cylindrical with a height of at least 1.75 inches; the inner diameter describes a cylinder, the base of which has an area of 4.37 in$^2$. The bottom of the test cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder. A spacer weighing about 60 grams and having a circular diameter of about 2.36 inches is made to fit within the AULC test cup without binding. The spacer is formed with multiple cylinder holes of about 9 mm diameter, providing an open area of about 52%. A 100 mesh screen is adhered to the bottom of the spacer in a similar manner as the mesh which is attached to the bottom of the test cup or other suitable method. Weights are sized to fit on top of the spacer. The first weight should apply a load of 600 grams (in combination with the spacer), and the second weight, in combination with the first weight and the spacer disc, should apply a load of 1800 grams.

Additional equipment required includes a vacuum trap for liquid that is suctioned out of the composite material at the end of the test, shallow dishes such as Petri dishes or plastic weighing boats suitable for holding an excess amount of liquid than will be imbibed by the sample, and a thin mesh screen with a thickness between 0.3 mm and 0.75 mm and a mesh size of about 1.2 mm. The vacuum trap is adapted to apply vacuum to an area matching the dimensions of the bottom of the AULC testing cup (for example, a larger vacuum area may be selectively screened with a relatively impermeable material except in an area matching the dimensions of the bottom of the AULC cup). The vacuum applied is about 27 inches of mercury.

Composite samples are cut to fit inside the AULC testing cup. Airlaid or nonwoven-based materials are cut into circles 2.35 inches in diameter. Airformed samples are cut or formed into circles, each with a diameter of 2.312 inches.

To carry out the test, test cup and spacer should be clean and dry. The test cup and spacer to be used in each trial should be weighed together (Measurement 1), and the mass recorded. The specimen is placed in the sample cup and the spacer is placed on top of the sample in the cup. The assembly is then weighed (Measurement 2), and the mass is recorded. The appropriate amount of weight is placed atop the spacer, if required. The spacer alone applies a force of 0.03 pounds per square inch of area (psia; the disc and first weight, with a net mass of 600 grams, apply a force of 0.3 psi, and the disc and both weights together, having a net mass of 1800 grams, apply a force of 0.9 psi).

The cup holding the specimen is placed in a pool of excess fluid in the shallow dish on top of the mesh screen and a one hour timer is started immediately. The level of fluid in the dish is maintained between about 1 mm and 2 mm depth. Following one hour, the specimen is removed from the fluid bath. Any fluid that may have accumulated atop the specimen should be poured off without displacing any weights atop the spacer disc. The specimen assembly is then placed on the vacuum box, with any weights still in place. Vacuum is applied to the sample for 30 seconds.

Any weights atop the spacer are then removed from the assembly and the assembly is weighed again (Measurement 3). The mass is recorded.

The dry weight of the specimen is calculated by subtracting Measurement 1 from Measurement 2. The amount of fluid absorbed by the specimen is calculated by subtracting Measurement 2 from Measurement 3. The absorbency under load of the composite material is calculated as the amount of fluid absorbed divided by the dry weight of the specimen.

At least three specimens of each sample should be measured, and the absorbency under load values should be averaged to obtain an overall absorbency under load for the composite sample.

TEST METHOD FOR DETERMINING STIFFNESS

A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-E manufactured by Teledyne Gurley, a business having offices in Troy, N.Y. For purposes of the present invention, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

TEST METHOD FOR DETERMINING ABSORBENT CAPACITY

Centrifuge Retention Capacity: As used herein, the Centrifugal Retention Capacity (CRC) is a measure of the absorbent capacity of the superabsorbent material retained after being subjected to centrifugation under controlled conditions. The CRC can be measured by placing a sample of the material to be tested into a water-permeable bag which will contain the sample while allowing the test solution (0.9 percent NaCl solution) to be freely absorbed by the sample. A heat-sealable tea bag material (available from Dexter Nonwovens of Windsor Locks, Conn., U.S.A., as item #11697) works well for most applications. The bag is formed by folding a 5-inch by 3-inch sample of the bag material in half and heat sealing two of the open edges to form a 2.5-inch by 3-inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. A sample size is chosen such that the teabag does not restrict the swelling of the material, generally with dimensions smaller than the sealed bag area (about 2-inch by 2.5-inch). Three sample bags are tested for each material.

The sealed bags are submerged in a pan of 0.9 percent NaCl solution. After wetting, the samples remain in the solution for 60 minutes, at which time they are removed from the solution and temporarily laid on a non-absorbent flat surface.

The wet bags are then placed into the basket of a suitable centrifuge capable of subjecting the samples to a g-force of 350. (A suitable centrifuge is a Heraeus LABOFUGE 400, Heraeus Instruments, part number 75008157, available from Heraeus Infosystems GmbH, Hanau, Germany). The bags are centrifuged at a target of 1600 rpm, but within the range of 1500–1900 rpm, for 3 minutes (target g-force of 350). The bags are removed and weighed. The amount of fluid absorbed and retained by the material, taking into account the fluid retained by the bag material alone, is the Centrifugal Retention Capacity of the material, expressed as grams of fluid per gram of material.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. An absorbent binder composition, comprising:
   at least 15 mass percent monoethylenically unsaturated polymer selected from a group consisting of carboxylic acid, carboxylic acid salts, sulphonic acid, sulphonic acid salts, phosphoric acid, and phosphoric acid salts; and
   an acrylate or methacrylate ester that contains an alkoxysilane functionality.

2. The absorbent binder composition of claim 1, wherein, upon exposure to water, the alkoxysilane functionality forms a silanol functional group which condenses to form a crosslinked polymer.

3. The absorbent binder composition of claim 1, wherein the monoethylenically unsaturated polymer comprises a carboxyl group-containing monomer.

4. The absorbent binder composition of claim 1, wherein the monoethylenically unsaturated polymer comprises a carboxylic acid anhydride group-containing monomer.

5. The absorbent binder composition of claim 1, wherein the monoethylenically unsaturated polymer comprises a carboxylic acid salt-containing monomer.

6. The absorbent binder composition of claim 1, wherein the monoethylenically unsaturated polymer comprises a sulfonic acid group-containing monomer.

7. The absorbent binder composition of claim 1, wherein the monoethylenically unsaturated polymer comprises an amide group-containing monomer.

8. The absorbent binder composition of claim 1, wherein the monoethylenically unsaturated polymer comprises between about 20% and about 99.9% by weight of the absorbent binder composition.

9. The absorbent binder composition of claim 1, wherein the monoethylenically unsaturated polymer comprises between about 25% and about 90% by weight of the absorbent binder composition.

10. The absorbent binder composition of claim 1, wherein the monoethylenically unsaturated polymer comprises between about 30% and about 80% by weight of the absorbent binder composition.

11. The absorbent binder composition of claim 1, wherein the monoethylenically unsaturated polymer comprises between about 50% and about 70% by weight of the absorbent binder composition.

12. The absorbent binder composition of claim 1, wherein the acrylate or methacrylate ester comprises a monomer containing a trialkoxy silane functional group.

13. The absorbent binder composition of claim 12, wherein the monomer comprises at least one of a group consisting of methacryloxypropyl trimethoxy silane, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy)silane.

14. The absorbent binder composition of claim 12, wherein the monomer comprises at least 0.1% by weight of the absorbent binder composition.

15. The absorbent binder composition of claim 12, wherein the monomer comprises between about 0.1% and about 20% by weight of the absorbent binder composition.

16. The absorbent binder composition of claim 12, wherein the monomer comprises between about 1.0% and about 10% by weight of the absorbent binder composition.

17. The absorbent binder composition of claim 12, wherein the monomer comprises between about 1.5% and about 5.5% by weight of the absorbent binder composition.

18. The absorbent binder composition of claim 1, comprising a long chain, hydrophilic, monoethylenically unsaturated ester having from 1 to 13 ethylene glycol units.

19. The absorbent binder composition of claim 18, wherein the monoethylenically unsaturated ester comprises up to about 75% by weight of the absorbent binder composition.

20. The absorbent binder composition of claim 18, wherein the monoethylenically unsaturated ester comprises between about 10% and about 60% by weight of the absorbent binder composition.

21. The absorbent binder composition of claim 18, wherein the monoethylenically unsaturated ester comprises between about 20% and about 50% by weight of the absorbent binder composition.

22. The absorbent binder composition of claim 18, wherein the monoethylenically unsaturated ester comprises between about 30% and about 40% by weight of the absorbent binder composition.

23. The absorbent binder composition of claim 1, wherein the absorbent binder composition has a glass transition temperature below 30 degrees Celsius.

24. The absorbent binder composition of claim 1, wherein the absorbent binder composition has a glass transition temperature below 10 degrees Celsius.

25. The absorbent binder composition of claim 1, wherein the absorbent binder composition can absorb at least 80% of its dry weight of 0.9% saline solution with no load applied during swelling.

26. The absorbent binder composition of claim 1, wherein the absorbent binder composition has a Centrifugal Retention Capacity of about 80% to about 4000% of its dry weight of 0.9% saline solution.

27. The absorbent binder composition of claim 1, wherein the absorbent binder composition has a Centrifugal Retention Capacity of about 80% to about 1500% of its dry weight of 0.9% saline solution.

28. The absorbent binder composition of claim 1, wherein the absorbent binder composition has a Centrifugal Retention Capacity of about 100% to about 900% of its dry weight of 0.9% saline solution.

29. The absorbent binder composition of claim 1, wherein the absorbent binder composition has a Centrifugal Retention Capacity of about 300% to about 700% of its dry weight of 0.9% saline solution.

30. An absorbent article, comprising the absorbent binder composition of claim 1 applied to a substrate.

31. An absorbent binder composition, comprising:
at least 15 mass percent monoethylenically unsaturated polymer selected from a group consisting of carboxylic acid, carboxylic acid salts, sulphonic acid, sulphonic acid salts, phosphoric acid, and phosphoric acid salts; and
an acrylate or methacrylate ester that contains a group readily transformed into a silanol functionality by subsequent reaction with water.

32. The absorbent binder composition of claim 31, wherein the monomer comprises at least one of a group consisting of chlorosilane and acetoxysilane.

33. The absorbent binder composition of claim 32, wherein the monomer comprises at least 0.1% by weight of the absorbent binder composition.

34. The absorbent binder composition of claim 32, wherein the monomer comprises between about 0.1% and about 20% by weight of the absorbent binder composition.

35. The absorbent binder composition of claim 32, wherein the monomer comprises between about 1.0% and about 10% by weight of the absorbent binder composition.

36. The absorbent binder composition of claim 32, wherein the monomer comprises between about 1.5% and about 5.5% by weight of the absorbent binder composition.

37. An absorbent binder composition, comprising:
at least 15 mass percent monoethylenically unsaturated polymer selected from a group consisting of carboxylic acid, carboxylic acid salts, sulphonic acid, sulphonic acid salts, phosphoric acid, and phosphoric acid salts; and
a monomer capable of co-polymerization which by subsequent reaction can incorporate a silane functional group capable of reaction with water to form a silanol group.

38. The absorbent binder composition of claim 37, wherein, upon exposure to water, the monomer capable of co-polymerization and subsequent reaction, can incorporate a silane functional group that forms a silanol functional group which condenses to form a crosslinked polymer.

39. The absorbent binder composition of claim 37, wherein the monoethylenically unsaturated polymer comprises a carboxyl group-containing monomer.

40. The absorbent binder composition of claim 37, wherein the monoethylenically unsaturated polymer comprises a carboxylic acid anhydride group-containing monomer.

41. The absorbent binder composition of claim 37, wherein the monoethylenically unsaturated polymer comprises a carboxylic acid salt-containing monomer.

42. The absorbent binder composition of claim 37, wherein the monoethylenically unsaturated polymer comprises a sulfonic acid group-containing monomer.

43. The absorbent binder composition of claim 37, wherein the monoethylenically unsaturated polymer comprises an amide group-containing monomer.

44. The absorbent binder composition of claim 37, wherein the monoethylenically unsaturated polymer comprises between about 20% and about 99.9% by weight of the absorbent binder composition.

45. The absorbent binder composition of claim 37, wherein the monoethylenically unsaturated polymer comprises between about 25% and about 90% by weight of the absorbent binder composition.

46. The absorbent binder composition of claim 37, wherein the monoethylenically unsaturated polymer comprises between about 30% and about 80% by weight of the absorbent binder composition.

47. The absorbent binder composition of claim 37, wherein the monoethylenically unsaturated polymer comprises between about 50% and about 70% by weight of the absorbent binder composition.

48. The absorbent binder composition of claim 37, wherein the monomer capable of co-polymerization comprises an amine.

49. The absorbent binder composition of claim 48, wherein the amine is subsequently reacted with (3-chloropropyl)trimethoxysilane.

50. The absorbent binder composition of claim 37, wherein the monomer capable of co-polymerization comprises an alcohol.

51. The absorbent binder composition of claim 50, wherein the alcohol is subsequently reacted with tetramethoxysilane.

52. The absorbent binder composition of claim 37, wherein the monomer comprises at least 0.1% by weight of the absorbent binder composition.

53. The absorbent binder composition of claim 37, wherein the monomer comprises between about 0.1% and about 20% by weight of the absorbent binder composition.

54. The absorbent binder composition of claim 37, wherein the monomer comprises between about 1.0% and about 10% by weight of the absorbent binder composition.

55. The absorbent binder composition of claim 37, wherein the monomer comprises between about 1.5% and about 5.5% by weight of the absorbent binder composition.

56. The absorbent binder composition of claim 37, comprising a long chain, hydrophilic, monoethylenically unsaturated ester having from 1 to 13 ethylene glycol units.

57. The absorbent binder composition of claim 56, wherein the monoethylenically unsaturated ester comprises up to about 75% by weight of the absorbent binder composition.

58. The absorbent binder composition of claim 56, wherein the monoethylenically unsaturated ester comprises between about 10% and about 60% by weight of the absorbent binder composition.

59. The absorbent binder composition of claim 56, wherein the monoethylenically unsaturated ester comprises between about 20% and about 50% by weight of the absorbent binder composition.

60. The absorbent binder composition of claim 56, wherein the monoethylenically unsaturated ester comprises between about 30% and about 40% by weight of the absorbent binder composition.

61. The absorbent binder composition of claim 37, wherein the absorbent binder composition has a glass transition temperature below 30 degrees Celsius, as measured by Differential Scanning Calorimetry.

62. The absorbent binder composition of claim 37, wherein the absorbent binder composition has a glass transition temperature below 10 degrees Celsius, as measured by Differential Scanning Calorimetry.

63. The absorbent binder composition of claim 37, wherein the absorbent binder composition has a Centrifugal Retention Capacity of at least 80% of its dry weight of 0.9% saline solution.

64. The absorbent binder composition of claim 37, wherein the absorbent binder composition has a Centrifugal Retention Capacity of between about 80% and about 4000% of its dry weight of 0.9% saline solution.

65. The absorbent binder composition of claim 37, wherein the absorbent binder composition has a Centrifugal Retention Capacity of between about 80% and about 1500% of its dry weight of 0.9% saline solution.

66. The absorbent binder composition of claim 37, wherein the absorbent binder composition has a Centrifugal Retention Capacity of between about 100% and about 900% of its dry weight of 0.9% saline solution.

67. The absorbent binder composition of claim 37, wherein the absorbent binder composition has a Centrifugal Retention Capacity of between about 300% and about 700% of its dry weight of 0.9% saline solution.

68. An absorbent article, comprising the absorbent binder composition of claim 37 applied to a substrate.

* * * * *